(12) United States Patent
Magnusson et al.

(10) Patent No.: US 7,884,888 B2
(45) Date of Patent: *Feb. 8, 2011

(54) AUTOMATIC DARKENING FILTER WITH OFFSET POLARIZERS

(75) Inventors: Kristina M. Magnusson, Gagnef (SE); Kenneth Jarefors, Gagnef (SE); Per-Olav Dahlin, Borlange (SE)

(73) Assignee: 3M Innovative Properties Company, St. Paul, MN (US)

( * ) Notice: Subject to any disclaimer, the term of this patent is extended or adjusted under 35 U.S.C. 154(b) by 108 days.

This patent is subject to a terminal disclaimer.

(21) Appl. No.: 12/328,290

(22) Filed: Dec. 4, 2008

(65) Prior Publication Data

US 2009/0079886 A1 Mar. 26, 2009

Related U.S. Application Data

(63) Continuation of application No. 11/076,081, filed on Mar. 9, 2005, now Pat. No. 7,477,330.

(51) Int. Cl.
*G02F 1/1347* (2006.01)
*G02F 1/1335* (2006.01)

(52) U.S. Cl. .............. 349/14; 349/76; 349/81; 349/99; 349/103; 349/180

(58) Field of Classification Search .......... 349/13, 349/14, 74–77, 80, 81, 96, 99, 103, 179, 349/180; 351/41, 44, 45; 250/201.1, 206, 250/214 AL, 214 B, 215

See application file for complete search history.

(56) References Cited

U.S. PATENT DOCUMENTS

| | | |
|---|---|---|
| 2,423,320 A | 7/1947 | Hurley, Jr. |
| 2,761,046 A | 8/1956 | Herrick et al. |
| 3,137,784 A | 6/1964 | Kasemann |
| 3,245,315 A | 4/1966 | Marks et al. |
| 3,575,491 A | 4/1971 | Heilmeier |
| 3,731,986 A | 5/1973 | Fergason |
| 3,873,804 A | 3/1975 | Gordon |
| 3,881,808 A | 5/1975 | Gurtler et al. |
| 3,890,628 A | 6/1975 | Gurtler |

(Continued)

FOREIGN PATENT DOCUMENTS

DE 2315308 3/1972

(Continued)

OTHER PUBLICATIONS

A. Dore et al., "P-21: Low Twist Nematic and PWM Direct Addressing as a New Technique for Large LCD Public Information Boards," pp. 445-447, Eurodisplay, 2002.

(Continued)

*Primary Examiner*—David Nelms
*Assistant Examiner*—Tai Duong
(74) *Attorney, Agent, or Firm*—Emily M. Van Vliet

(57) ABSTRACT

A protective automatic darkening filter construction 10 includes two low twist liquid crystal cells 26, 30 interspersed between a series of offset polarizers 24, 28, 32. The resulting construction provides improved homogeneity in the dark state as viewed by the user over a large viewing angle. By reducing variations in shade, visibility through the filter may be improved.

14 Claims, 2 Drawing Sheets

U.S. PATENT DOCUMENTS

| | | | |
|---|---|---|---|
| 3,918,796 | A | 11/1975 | Fergason |
| 3,967,881 | A | 7/1976 | Moriyama et al. |
| 4,039,254 | A | 8/1977 | Harsch |
| 4,071,912 | A | 2/1978 | Budmiger |
| RE29,684 | E | 6/1978 | Gordon |
| 4,093,832 | A | 6/1978 | Isaacson et al. |
| 4,109,114 | A | 8/1978 | Baer et al. |
| 4,143,264 | A | 3/1979 | Gilbert et al. |
| 4,155,122 | A | 5/1979 | Budmiger |
| 4,237,557 | A | 12/1980 | Gordon |
| 4,240,709 | A | 12/1980 | Hornell |
| 4,279,474 | A | 7/1981 | Belgorod |
| 4,328,493 | A | 5/1982 | Shanks et al. |
| 4,385,806 | A | 5/1983 | Fergason |
| 4,436,376 | A | 3/1984 | Fergason |
| 4,540,243 | A | 9/1985 | Fergason |
| 4,556,289 | A | 12/1985 | Fergason |
| 4,560,239 | A | 12/1985 | Katz |
| 4,664,479 | A | 5/1987 | Hiroshi |
| RE32,521 | E | 10/1987 | Fergason |
| 4,710,694 | A | 12/1987 | Sutphin et al. |
| 4,728,173 | A | 3/1988 | Toth |
| 4,759,608 | A | 7/1988 | Yang |
| 4,821,292 | A | 4/1989 | Childress |
| 4,844,569 | A | 7/1989 | Wada et al. |
| 4,853,973 | A | 8/1989 | Boochard |
| 4,863,244 | A | 9/1989 | Fuerthbauer et al. |
| 4,875,235 | A | 10/1989 | Kuhlman |
| 4,896,947 | A | 1/1990 | Leenhouts |
| 4,952,030 | A | 8/1990 | Nakagawa et al. |
| 5,015,086 | A | 5/1991 | Okaue et al. |
| 5,074,647 | A | 12/1991 | Fergason et al. |
| 5,113,270 | A | 5/1992 | Fergason |
| 5,140,707 | A | 8/1992 | Johnson |
| 5,184,156 | A | 2/1993 | Black et al. |
| 5,191,468 | A | 3/1993 | Mases |
| 5,208,688 | A | 5/1993 | Fergason et al. |
| 5,248,880 | A | 9/1993 | Fergason |
| 5,252,817 | A | 10/1993 | Fergason et al. |
| 5,515,186 | A | 5/1996 | Fergason et al. |
| 5,533,206 | A | 7/1996 | Petrie et al. |
| 5,751,258 | A | 5/1998 | Fergason et al. |
| 5,825,441 | A | 10/1998 | Hornell et al. |
| 6,097,451 | A | 8/2000 | Palmer et al. |
| 6,185,736 | B1 | 2/2001 | Ueno |
| D517,744 | S | 3/2006 | Lee et al. |
| D517,745 | S | 3/2006 | Lee et al. |
| D518,923 | S | 4/2006 | Curran et al. |
| D523,728 | S | 6/2006 | Lee et al. |
| D532,163 | S | 11/2006 | Curran et al. |
| 7,197,774 | B2 | 4/2007 | Curran et al. |
| 7,477,330 | B2 | 1/2009 | Magnusson et al. |
| 2001/0017681 | A1* | 8/2001 | Hornell et al. ............... 349/117 |
| 2006/0101552 | A1 | 5/2006 | Lee et al. |
| 2006/0107431 | A1 | 5/2006 | Curran et al. |

FOREIGN PATENT DOCUMENTS

| | | |
|---|---|---|
| DE | 35615 | 5/1973 |
| DE | 2742211 | 5/1984 |
| DE | 3842824 | 6/1990 |
| DE | 3503958 | 5/1993 |
| EP | 0005417 | 4/1979 |
| EP | 0157744 | 10/1985 |
| EP | 0335056 | 3/1988 |
| EP | 0349665 | 1/1990 |
| FR | 2530039 | 1/1984 |
| GB | 325586 | 2/1930 |
| GB | 1430183 | 3/1976 |
| JP | 55-92276 | 7/1980 |
| JP | 59-111102 | 6/1984 |
| JP | 4338732 | 11/1992 |
| RU | 2077068 C1 | 4/1997 |
| RU | 2082209 C1 | 6/1997 |
| RU | 2154851 | 8/2000 |
| SE | 7312733 | 4/1974 |
| SE | 7608690 | 2/1978 |
| WO | WO 88/05926 | 8/1988 |
| WO | WO 90/14611 | 11/1990 |
| WO | WO 90/14809 | 12/1990 |
| WO | WO 95/29428 | 11/1995 |
| WO | WO 97/15255 | 5/1997 |
| WO | WO 2004/053586 | 6/2004 |
| WO | WO 2004/102265 | 11/2004 |

OTHER PUBLICATIONS

K.H. Yang, "Two-Domain 80°-Twisted Nematic Liquid Crystal Display for Grayscale Applications," Jpn. J. Applied Physics, vol. 31, pp. L1603-L1605, Part 2, No. 11B, Nov. 15, 1992.

* cited by examiner

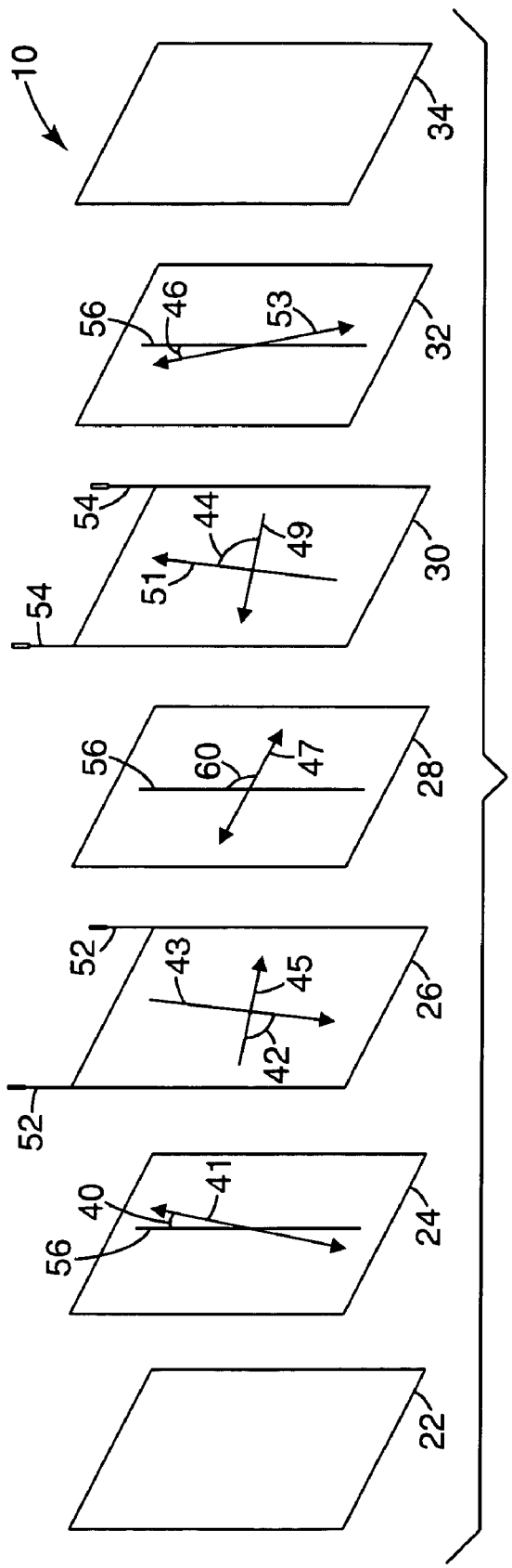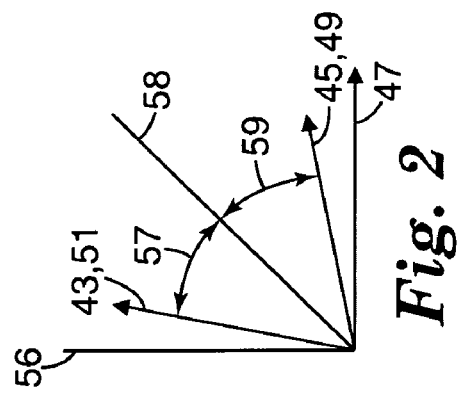

AUTOMATIC DARKENING FILTER WITH OFFSET POLARIZERS

CROSS REFERENCE TO RELATED APPLICATIONS

This application is a continuation of U.S. application Ser. No. 11/076,081, filed Mar. 9, 2005 now U.S. Pat. No. 7,477,330, the disclosure of which is incorporated by reference in its entirety herein.

The present invention pertains to an automatic darkening liquid crystal protective shield or filter that can be used on a welding helmet to filter light incident from a welder's torch.

BACKGROUND

Automatic darkening liquid crystal protective shields, also known as automatic darkening filters, or ADFs, are often constructed from a combination of polarizing filters and layers of liquid crystals. Examples of such filters are described in U.S. Pat. Nos. 6,097,451 and 5,825,441, both to Hörnell and Palmer.

The ADFs change from a light (transparent) state to a darker (nearly opaque) state in response to a control signal. For applications like welding where protection from intense levels of incident light is desired, the filters are normally mounted in a facemask, and the control signal is initiated by incident light from the welding arc. The incident light strikes a detector on the welding helmet which in turn sends a signal to the ADF. In this way, the filter is clear or transparent when not subjected to the glare of the welding arc and darkens immediately when exposed to such glare. This enables a welder to perform a welding operation and also to perform tasks outside the welding area without removing the protective shield.

Conventional filters have one particular drawback, namely, the filter effect of the liquid crystal layers is angularly dependent. In other words, the viewing area as seen by the user may appear to darken unevenly. Variations in cell gap and unwanted birefringence in the adhesive layers or the polarizers may also reduce homogeneity, resulting in variations in shade over the viewing area of the welding filter.

SUMMARY OF THE INVENTION

The present invention provides a protective automatic darkening filter construction that addresses the problem of a non-homogeneity in the viewing area. The construction provides the user with a more even shade in the dark state over a large viewing angle. The inventive filter includes two low twist optically rotating liquid crystal cells interspersed between three polarizers. The twist angle of the liquid crystal cells is less than 90 degrees. The two outside polarizers (the first and third polarizers) have polarization orientations that are offset from a normal axis to the polarization direction of the second (center) polarizer.

In one embodiment, the present invention is directed to a device that comprises first, second and third polarizers, and first and second low twist liquid crystal cells, where each liquid crystal has a twist angle of less than 90 degrees. The first low twist liquid crystal cell is disposed between the first and second polarizers, and the second low twist liquid crystal cell is disposed between the second and third polarizers. The polarization orientation of at least one of the first or third polarizers is offset from a normal axis to a polarization orientation of the second polarizer.

In another embodiment, the present invention is directed to an automatic darkening filter, that includes a welding facemask that has a switchable filter mounted therein. The automatic darkening filter also includes a sensor that detects incident light and control circuitry that receives signals from the sensor corresponding to the presence or absence of incident light. The control circuitry causes a voltage to be applied to the switchable filter in response to signal indicative of the presence of incident light. The switchable filter includes first, second and third polarizers, and first and second low twist liquid crystal cells, each having a twist angle of less than 90 degrees. The first low twist liquid crystal cell is disposed between the first and second polarizers. The second low twist liquid crystal cell is disposed between the second and third polarizers. The polarization orientation of at least one of the first or third polarizers is offset from a normal axis to a polarization orientation of the second polarizer.

The present invention differs from known automatic darkening filters in that at least one of the first and third polarizers are offset from a normal axis to a polarization orientation of the second polarizer. By offsetting the polarization orientation of at least one of the first or third polarizers, a more homogeneous shade in the dark state may be obtained. Offsetting the polarization orientation of one or both of the first or third polarizers allows a small amount of light to leak through the filter, causing an overall softening effect that reduces variations in shade as viewed through the filter. By reducing variations in shade, visibility through the filter may be improved. Improvements in visibility can be particularly beneficial to welders because they need to see in detail the objects on which they are working.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is an exploded view of an example embodiment of a protective switchable filter construction 10 according to the present invention.

FIG. 2 is a diagram showing one example alignment of the polarizers and liquid crystal cells for the switchable filter 10 of FIG. 1.

DETAILED DESCRIPTION OF PREFERRED EMBODIMENTS

Figure 3:
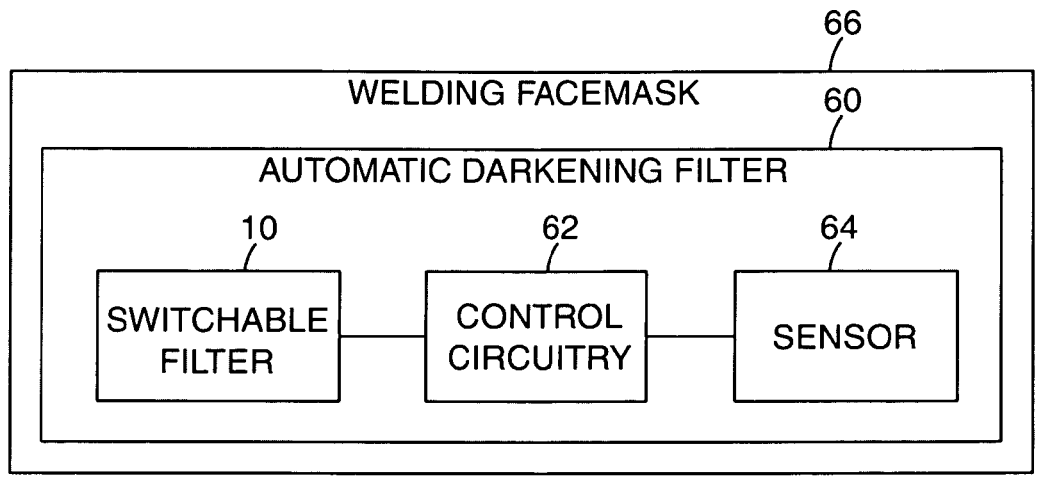
FIG. 3 is a block diagram of the switchable filter 10 of FIG. 1 mounted in an automatic darkening filter 60.

FIG. 1 is an exploded view of an example embodiment of a switchable filter construction 10 that is useful for automatic darkening filter applications. The outermost component is an interference filter 22, which filter functions in part to eliminate UV light and IR light and limits the wavelength range. Filter 10 also includes a first polarizing filter 24, a first optically rotating liquid crystal cell 26, a second polarizing filter 28, a second optically rotating liquid crystal cell 30, and a third polarizing filter 32. The arrangement may optionally also include a so-called guest-host-cell 34.

First and second liquid crystal cells 26 and 30 are low twist liquid crystal cells. As used in this document, the term "low twist" means having a twist angle of less than 90 degrees. For example, at least one of first and second liquid crystal cell 26 or 30 has a twist angle of less than 90 degrees, typically zero or 1 to 89 degrees. More specifically, the twist angle of at least one of first and second liquid crystal cells may be between about 20 degrees and about 85 degrees. The liquid crystal cells 26 and 30 are provided with connectors 52 and 54, respectively, by which a control voltage may be applied.

Each of the first, second, and third polarizers 24, 28 and 32, respectively, have associated polarization orientations indicated by arrows in FIG. 1. As used in this document, the term "polarizer" means a polarizing filter that transmits light waves along one axis and absorbs them along the other. Typically, the transmitting and absorbing axes of polarization are oriented at 90 degrees to each other. These axes of polarization, or polarization orientations, of first polarizer 24 and third polarizer 32 may be described with respect to the orientation of second polarizer 28. Second polarizer 28 has a polarization orientation 47. Normal axis 56 is perpendicular to polarization orientation 47 of polarizer 28. In other words, the angle between normal axis 56 and polarization orientation 47 is 90 degrees in the embodiment shown in FIG. 1. The polarization orientations of first polarizer 24 and third polarizer 32 are both "offset" from normal axis 56. In other words, polarization orientation 41 of first polarizer 24 is offset from normal axis 56 by an offset angle 40 (hereinafter first offset angle 40). Similarly, polarization orientation 53 of third polarizer 32 is offset from normal axis 56 by an offset angle 46 (hereinafter second offset angle 46). Possible offsets provided by first and second offset angles 40 and 46 may be between 1 degree and 20 degrees. In one embodiment, the first and second offset angles 40 and 46 may be between 2 degrees and 8 degrees.

FIG. 1 further shows that both first polarizer 24 and third polarizer 32 are offset from normal axis 56. In some embodiments, however, only one of first polarizer 24 or third polarizer 32 are offset from normal axis 56. For example, in one embodiment, polarization orientation 41 of first polarizer 24 is offset from normal axis 56, while polarization orientation 53 of third polarizer 32 is substantially parallel with normal axis 56. In another embodiment, polarization orientation 41 of first polarizer 24 may be substantially parallel with normal axis 56, while polarization orientation 53 of third polarizer 32 is offset from normal axis 56. Thus, a polarization orientation of at least one of first polarizer 24 or third polarizer 32 is offset from normal axis 56.

First offset angle 40 may be offset from normal axis 56 in a clockwise, or positive, direction, while second offset angle 46 may be offset from normal axis 56 in a counterclockwise, or negative, direction. The direction of first and second offset angles 40 and 46 may be reversed, or, in some embodiments, they may be offset in the same direction (e.g., either both positive or both negative). The magnitude of first and second offset angles 40 and 46 may be the same in some embodiments, or may be different in other embodiments.

Liquid crystal cells 26 and 30 are "low twist" cells. That is, they have a twist angle of less than 90 degrees. A typical construction for this type of low twist cell consists of a twisted nematic (TN) type of liquid crystal material positioned between glass plates. The inwardly facing glass plates of the liquid crystal cells are provided with transparent electrically conductive electrode layers (e.g., indium tin oxide layers) on which there is applied, for instance, a polyimide layer that has been treated mechanically, such as by brushing or rubbing, in specific alignment directions. The resulting structure in the liquid crystal defining surfaces, forces the nematic molecules to take specific angular positions so that the molecules are twisted through their respective twist angle between the defining surfaces. In an electrically non-activated state (with no voltage applied), the polarization plane is rotated as light passes through the cell and the filter becomes transparent. The orientation of the nematic liquid crystal molecules can be controlled by applying an electric field between the defining surfaces. Application of a voltage creates an electric field between the defining surfaces. The nematic liquid crystal molecules align with the electric field perpendicular to the defining surfaces, rather than parallel to them, and the cell achieves a darkened state. Thus, when a control voltage is applied to the low twist cells, a filter effect is obtained. The degree of rotation of the nematic molecules may be controlled by varying the control voltage, and thus the corresponding filter effect may also be controlled. The result is that liquid crystal cells 26 and 30 are in a light state in the absence of an applied voltage is and are in a dark state in the presence of an applied voltage.

Guest-host-cell 34 may include a nematic liquid crystal, whose molecules and atoms may be aligned parallel to normal axis 56 in polarizer 28. A prepared glass surface can assist in this alignment. An inmixed pigment having ordered anisotropic absorption is highly absorbent in the aligned state. When a voltage is applied, the molecules of the nematic crystal position themselves at right angles to the prepared surfaces, causing the molecules of the pigment to move to positions in which the least amount of light is absorbed. Guest-host-cell 34 therefore provides a filter effect in the absence of an applied voltage, whereas the liquid crystal cells 26 and 30 are light transparent in the absence of an applied voltage. In this way, filter 10 provides some minimal level of protection and safety to the user in the event of an unintended voltage loss.

In the embodiment shown in FIG. 1, the corresponding alignment directions of the liquid crystal cells 26 and 30 are arranged substantially parallel to and oriented asymmetrically with respect to one another. For example, the alignment direction 45 of liquid crystal cell 26 is arranged substantially parallel to and oriented asymmetrically (i.e., in an opposite direction) with respect to alignment direction 49 of liquid crystal cell 30. Similarly, alignment direction 43 of liquid crystal cell 26 is arranged substantially parallel to and oriented asymmetrically with respect to alignment direction 51 of liquid crystal cell 30. This asymmetric orientation is illustrated by the opposite pointing arrows indicating the alignment directions 43, 45 and 49, 51 in FIG. 1.

FIG. 2 is a diagram that shows one example of how first liquid crystal cell 26, second polarizer 28, and second liquid crystal cell 30 may be arranged with respect to one another. FIG. 2 shows how the normal axis 56 and polarization orientation 47 of second polarizer 28 are perpendicular to each other as described above. Bisector 58 bisects the angle between polarization orientation 47 and normal axis 56. Thus, bisector 58 forms a 45 degree angle with polarization orientation 47 and normal axis 56 in this example. To optimize performance in the light state, alignment directions 45, 43 and 49, 51 of liquid crystal cells 26 and 30, respectively, may be arranged symmetrically with respect to bisector 58. For example, if the twist angle of liquid crystal cells 26 and 30 is equal to 70 degrees, then alignment directions 45 and 43 would be located symmetrically 35 degrees about bisector 58. Similarly, alignment directions 49 and 51 would also be located symmetrically 35 degrees about bisector 58. Thus, in this example, the angle 57 between alignment directions 43, 51 and bisector 58 is 35 degrees, as is the angle 59 between alignment directions 45, 49 and bisector 58. Stated another way, the angle between normal axis 56 and alignment directions 43, 51 would be 10 degrees, and the angle between normal axis 56 and alignment directions 45, 49 would be 80 degrees in this example.

Although a symmetric orientation may optimize the light state, other orientations may also be used, and the present invention is not limited to the arrangements shown and described herein with respect to FIGS. 1 and 2. Many other configurations are also possible without departing from the scope of the present invention.

FIG. 3 is a block diagram of an automatic darkening filter (ADF) 60. Automatic darkening filter 60 includes a switchable filter 10 that has offset polarizers of the type described above with respect to FIGS. 1 and 2. Switchable filter 10 is mounted in a welding facemask 66 that would be worn by the user during a welding procedure or other situation where protection of the type provided by switchable filter 10 is desired. ADF 60 also includes a sensor 64 for detecting light incident upon the front surface of filter 10, such as a welding arc. Control circuitry 62 receives signals from sensor 64 corresponding to the presence or absence of incident light and causes corresponding control voltages to be applied to filter 10, thus controlling the degree of shade provided by filter 10. When the presence of a welding arc or other source of incident light is detected by sensor 64, for example, control circuitry 62 may cause a control voltage to be applied to liquid crystal cells 26 and 30 while eliminating the voltage to guest-host cell 34. This causes the filter to darken and protect the user from the glare of the welding arc. In the absence of a welding arc or other source of incident light, control circuitry 62 may reduce or eliminate the applied voltage to liquid crystal cells 26 and 30, thus causing the filter to become more open to light. This enables a welder to perform a welding operation and also to perform tasks outside the welding area without removing the protective facemask. In addition, the filter construction described herein results in increased homogeneity in the dark state as seen by the user over a large angular range.

The switchable filter 10, sensor 64, and control circuitry 62 are typically supported on a helmet shell of a welding facemask 66 as a unit, typically a replaceable unit that is mounted in the shell directly in front of the wearer's eyes when the helmet is worn by the user. The unit may take the form of a rectangular (or other shaped) frame or housing that supports the filter, sensor, and circuitry. Examples of helmet shells may be seen, for example, in U.S. Pat. Nos. 6,185,739, 5,533,206, 5,191,468, 5,140,707, 4,875,235, and 4,853,973. The welding helmets also can have clean air supplied to their interior and thus may include a face seal to separate a breathing zone from the ambient air. An example of such a face seal is shown in U.S. patent application Ser. Nos. 10/987,512, 10/987,641, 10/988,789, 29/217,155, 29/217,153, 29/217,154, 29/217,107, 29/217,156.

One measure of the filter effect is the so-called Shade Number. Shade Number, S is related to luminous transmittance, TL (expressed as a fraction) by the following equation:

$$S=1+7/3\times 10 \log(1/TL).$$

A filter arrangement of the type described herein may change from a filter effect of about Shade 3.3 in the light state to values ranging from about Shade 9 to about Shade 13 in the dark state. The filter effect may change by varying the applied voltage from about 2.0 V to about 4.5 V.

Figure 4:
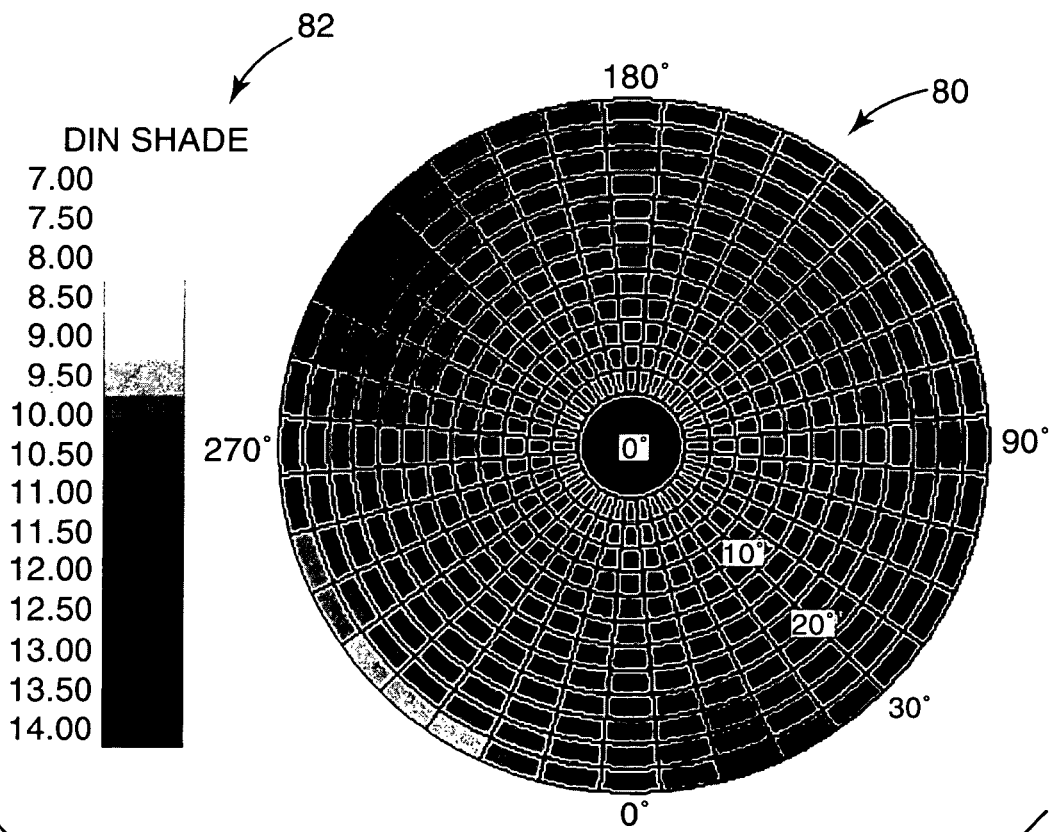
FIG. 4 is a polar diagram that illustrates the filter effect at different viewing angles for the switchable filter construction of FIG. 1.

FIG. 4 is a polar diagram 80 showing the Shade value at various viewing angles. FIG. 4 was measured using a switchable filter construction like that shown in FIG. 1, with the first polarizer 24 having an offset angle of 6 degrees measured in a clockwise direction, third polarizer 32 having an offset angle of 6 degrees measured in the counterclockwise direction, and liquid crystal cells 26 and 30 having a twist angle of 80 degrees. The outermost circle on polar diagram 80 represents a deviation of 30 degrees from a perpendicular angle of incidence (indicated at the center of the diagram). The diagram was produced in a stepping machine with the inclination taken in steps of 2.5 degrees and with an azimuth step of 10 degrees. Domains where every gray level represents an equal filter effect have been produced in Shade steps of 0.5. The DIN shade scale is indicated by reference numeral 82. Because the twist angle of the liquid crystal cells 26 and 30 differs from 90 degrees, and because the orientations of the first and third polarizers 24 and 32 are offset, the filter effect in the dark state is more uniform over varying angles of view than conventional filter constructions.

The measurements involved the use of two identical liquid crystal cells. In that type of embodiment, both liquid crystal cells 26 and 30 can be driven with the same control voltage, and this control voltage can be varied to produce different densities and thus different degrees of shade in the dark state. This provision may simplify the electronics that are required.

The liquid crystal cells 26 and 30, however, need not be identical. In one embodiment, for example, a 90 degree twist liquid crystal cell and low twist cell having a twist of between 20 degrees to 85 degrees may be arranged between offset polarizers. In another embodiment, two low twist cells each having different degrees of twist may be arranged between offset polarizers. Different cells may be combined so as to achieve an optimized total solution, depending upon the desired end result. For instance, it is possible to combine symmetrically and asymmetrically mounted liquid crystal cells, cells of different twist angles and thicknesses, etc.

All of the patents and patent applications cited above, including those cited in the Background Section, are incorporated by reference into this document in total.

Various embodiments of the invention have been described. These and other embodiments are within the scope of the following claims.

The invention claimed is:

1. A device, comprising:
a first, second and third polarizers; and
first and second low twist liquid crystal cells, each having a twist angle of one to less than 90 degrees, wherein the first low twist liquid crystal is disposed between the first and second polarizers, and wherein the second low twist liquid crystal is disposed between the second and third polarizers;
wherein a polarization orientation of the first polarizer is offset from a normal axis to a polarization orientation of the second polarizer by a first offset angle and a polarization orientation of the third polarizer is offset from the normal axis to the polarization orientation of the second polarizer by a second offset angle; and
wherein the second polarizer is adjacent to the first and second low twist liquid crystal cells.

2. The device of claim 1, wherein the twist angles of the first and second liquid crystal cells are between 20 degrees and 85 degrees.

3. The device of claim 1, wherein the first and second liquid crystal cells are substantially identical, and wherein the control voltage applied to each of the first and second liquid crystals is substantially identical.

4. The device of claim 1, wherein the magnitudes of the first and second offset angles are between 1 and 20 degrees.

5. The device of claim 1, wherein the magnitudes of the first and second offset angles are between 2 and 8 degrees.

6. The device of claim 1, wherein a polarization orientation of one of the first and third polarizers is offset from a normal axis to a polarization orientation of the second polarizer by a first offset angle measured in a clockwise direction and wherein a polarization orientation of the other one of the first and third polarizers is offset from the normal axis to the polarization orientation of the other of the second polarizer by a second offset angle measured in a counterclockwise direction.

7. The device of claim 6, wherein the first and second offset angles have magnitudes that are substantially equivalent.

8. The device of claim 1, wherein the first low twist liquid crystal cell includes corresponding first and second alignment directions, and wherein the first and second alignment directions are arranged substantially symmetrically with respect to a bisector of the polarization orientation of the second polarizer and a normal axis to the polarization orientation of the second polarizer.

9. The device of claim 1, wherein the second low twist liquid crystal cell includes corresponding first and second alignment directions, and wherein the first and second alignment directions are arranged substantially symmetrically with respect to a bisector of the polarization orientation of the second polarizer and a normal axis to the polarization orientation of the second polarizer.

10. An automatic darkening filter unit that comprises the device of claim 1, and further includes a sensor for sensing incident light from a welder's torch and a control circuitry that generates and delivers a signal to the device to cause the device to darken in response to the incident light.

11. A welder's helmet that comprises a shell and the automatic darkening filter unit of claim 10, the automatic darkening filter unit being supported by the shell such that the unit is disposed in front of a wearer's eyes when the welding helmet is being worn.

12. The welder's helmet of claim 11, wherein the automatic darkening filter unit is replaceable.

13. A device, comprising:
a welding facemask;
a switchable filter mounted in the welding facemask;
a sensor to detect incident light; and
control circuitry that receives signals from the sensor corresponding to presence or absence of incident light and that causes a voltage to be applied to the switchable filter in response to signal indicative of the presence of incident light;
wherein the switchable filter includes:
first, second and third polarizers; and
first and second low twist liquid crystal cells, each having a twist angle of one to less than 90 degrees, wherein the first low twist liquid crystal cell is disposed between the first and second polarizers, and wherein the second low twist liquid crystal cell is disposed between the second and third polarizers;
wherein a polarization orientation of the first polarizer is offset from a normal axis to a polarization orientation of the second polarizer by a first offset angle and a polarization orientation of the third polarizer is offset from the normal axis to the polarization orientation of the second polarizer by a second offset angle; and
wherein the second polarizer is adjacent to the first and second low twist liquid crystal cells.

14. The device of claim 13, wherein the first and second offset angles are between 2 degrees and 8 degrees.

* * * * *